United States Patent [19]
Shin

[11] Patent Number: 6,063,092
[45] Date of Patent: *May 16, 2000

[54] HEAT SET AND CRIMPING PROCESS TO OPTIMIZE STENT RETENTION

[75] Inventor: Mark Young Shin, San Diego, Calif.

[73] Assignee: Medtronic Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/056,274

[22] Filed: Apr. 7, 1998

[51] Int. Cl.⁷ ..................................................... A61F 11/00
[52] U.S. Cl. ........................................... 606/108; 606/194
[58] Field of Search ..................................... 606/108, 191, 606/194, 198, 195

[56] References Cited

U.S. PATENT DOCUMENTS

| | | |
|---|---|---|
| 4,434,797 | 3/1984 | Silander . |
| 4,732,152 | 3/1988 | Wallstén et al. . |
| 4,733,665 | 3/1988 | Palmaz . |
| 4,800,882 | 1/1989 | Gianturco . |
| 4,886,062 | 12/1989 | Wiktor . |
| 4,907,336 | 3/1990 | Gianturco . |
| 4,913,141 | 4/1990 | Hillstead . |
| 5,133,732 | 7/1992 | Wiktor . |
| 5,292,331 | 3/1994 | Bonneau .................................. 606/198 |
| 5,632,760 | 5/1997 | Sheiban et al. . |
| 5,643,278 | 7/1997 | Wijay . |
| 5,836,965 | 11/1998 | Jendersee et al. ....................... 606/198 |

*Primary Examiner*—Michael Buiz
*Assistant Examiner*—Vy Q. Bui

[57] ABSTRACT

A method for manufacturing a stent delivery catheter includes the step of crimping an expandable stent over an inflatable balloon to create a balloon-stent assembly. The balloon-stent assembly is then constrained by a covering tube and a shrink wrap which act together to prevent expansion of the stent when the balloon is pressurized. Next, the balloon is pressurized. In this configuration, the assembly is heated to permanently deform the balloon by embedding the stent into the balloon surface. The result is a stent delivery catheter system in which protrusions that are formed on the balloon surface are inserted into openings in the stent wall to enhance the retention forces acting between the balloon and the stent.

9 Claims, 4 Drawing Sheets

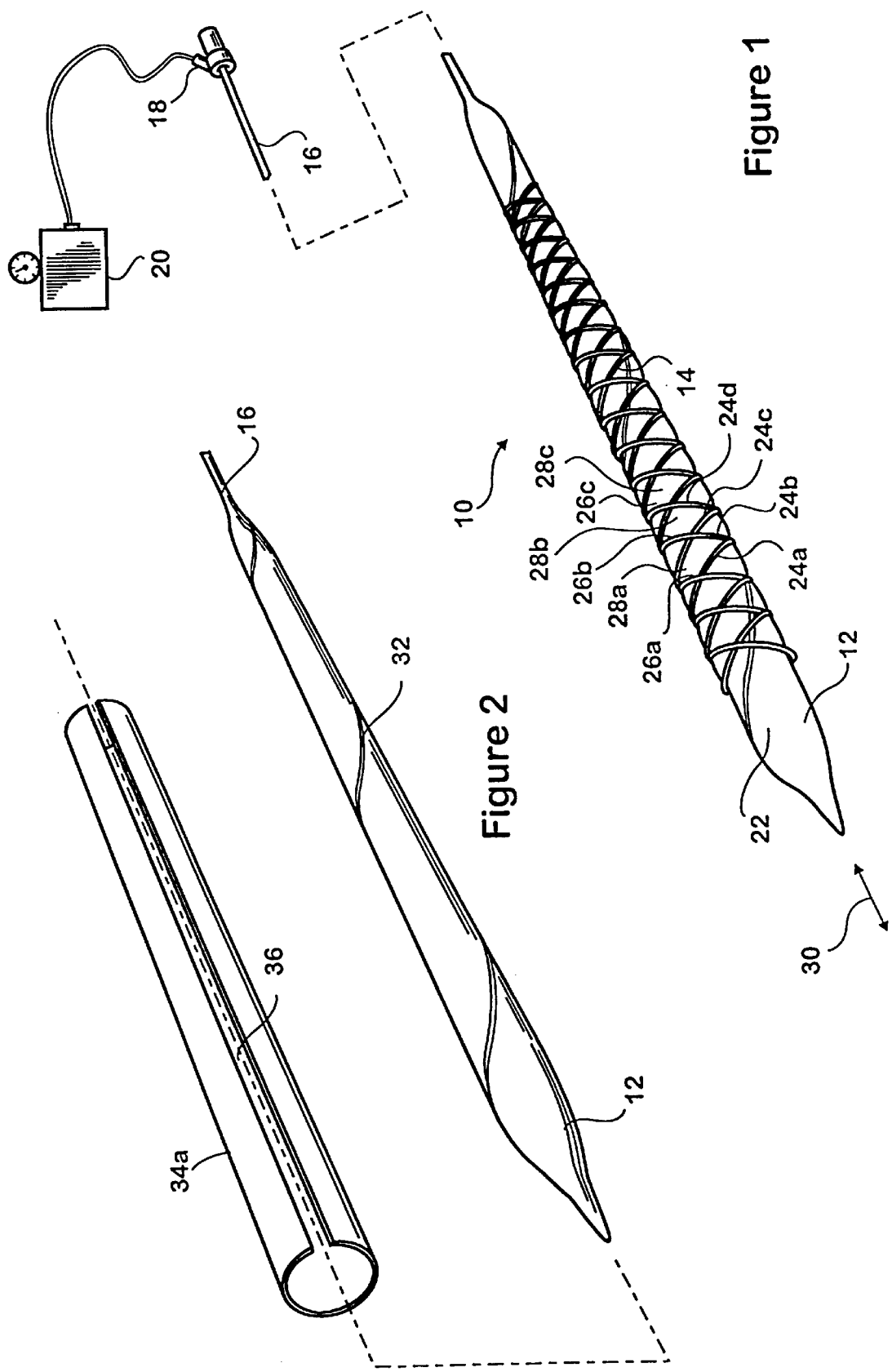

HEAT SET AND CRIMPING PROCESS TO OPTIMIZE STENT RETENTION

FIELD OF THE INVENTION

The present invention pertains generally to stent delivery catheter systems and their method of manufacture. More particularly, the present invention pertains to methods for enhancing the retention forces which are required for holding a stent on a balloon catheter prior to the delivery and emplacement of the stent at the site of a lesion in a patient. The present invention is particularly, but not exclusively, useful for creating a balloon structure which provides enhanced interactive cooperation between the balloon and the stent for the development of retention forces between the balloon and the catheter.

BACKGROUND OF THE INVENTION

The use of a stent to establish and maintain patency in an otherwise occluded vessel in the cardiovascular system of a patient has been a preferred surgical procedure for many years. By way of a general overview of such a procedure, the stent is delivered through the affected vessel to the site of the lesion causing the occlusion. At the lesion site, the stent is implanted to obviate the effects of the lesion. To do this, a balloon catheter is typically used as a delivery system. An example of such a stent, and a method for its use, is provided by U.S. Pat. No. 5,133,732 which issued to Wiktor for an invention entitled "Intravascular Stent," and which is assigned to the same assignee as the present invention.

In order to use a balloon catheter for a stent delivery system, the stent is positioned around the balloon with the stent in a compressed configuration. In its compressed configuration, the stent is designed to present the small profile that is necessary for advancement of the stent through the vessel of the patient. Once at the site of the lesion, the balloon is inflated to reconfigure the stent from its compressed configuration into an expanded configuration. This reconfiguration expands the stent against the lesion. The balloon is then deflated to disengage the balloon from the stent which has now been permanently reconfigured into its expanded configuration. Lastly, the balloon catheter is removed from the patient, while leaving the expanded stent in place at the site of the lesion.

When a balloon catheter is used as part of a stent delivery system, it is, of course, desirable for the stent to remain in position on the balloon catheter until such time as the balloon is inflated by the physician. It is, however, also desirable for the stent to be easily disengaged or detached from the balloon after the balloon has been inflated by the physician. As a practical matter, it is necessary to keep the stent from slipping off the balloon before the stent has been delivered to the site of the lesion.

It happens that the stent, and the balloon on which it is carried, are both elongated structures which generally define respective longitudinal axes. Accordingly, when the stent and balloon are joined together they are effectively coaxial. In this configuration, separation of the stent from the balloon is most likely to occur by movement of the stent over the balloon in an axial direction relative to the balloon. Consequently, a resistive retention force, which is axially aligned with the stent and balloon, and which acts between the stent and the balloon, will help prevent premature separation of the stent from the balloon.

Heretofore, in order to retain a stent on a balloon, many stent delivery systems have relied only on the forces which result when the stent is crimped onto the balloon. Consequently, the desired results of this crimping action has been two-fold. For one, this crimping is intended to compress the stent into a low profile configuration. For another, the crimping was intended to generate accompanying forces between the balloon and the stent which will hold the stent on the balloon. The crimping forces, however, are generally applied in a radial direction relative to the balloon and stent and, as such, do not specifically establish axially oriented retention forces. Thus, with only crimping, there are no designed axial forces which will prevent or inhibit axial movement of the stent over the balloon. The situation is only aggravated when a slippery, low friction, material is used for the manufacture of the balloon.

There are, of course, methods other than crimping which have been suggested for holding a stent on a balloon. For example, in U.S. Pat. No. 4,733,665, the catheter includes retaining ring members at the proximal and distal ends of the stent to assist in retaining it on the balloon. Also, U.S. Pat. No. 5,632,760 discloses bulges which are locked proximal and distal to the stent to hold the stent on the balloon. As another example, U.S. Pat. No. 5,643,278 discloses a sheath which is deployed over the stent to retain it during delivery. Additionally, this patent discloses use of a frangible glue to hold the stent on the balloon.

In light of the above, it is an object of the present invention to provide a stent delivery catheter system, and a method for manufacturing a stent delivery catheter, which enhances the interactive forces between the stent and the balloon that prevent or inhibit axial movement of the stent over the balloon before the balloon is inflated. Another object of the present invention is to provide a stent delivery catheter system, and a method for manufacturing a stent delivery catheter, which allows for easy disengagement of the balloon from the stent when the balloon subsequently deflated after having been inflated to expand and position the stent at the site of a lesion in a patient's vessel. Still another object of the present invention is to provide a stent delivery catheter system (and a method for manufacturing a stent delivery catheter) which is easy to use, simple to manufacture and comparatively cost effective.

SUMMARY OF THE PREFERRED EMBODIMENTS

In accordance with the present invention, a method for manufacturing a stent delivery catheter is provided that results in a system which has enhanced capabilities for holding a stent on a balloon catheter until the stent has been delivered and placed at a lesion site. Specifically, due to a structural interaction between the balloon of the balloon catheter and the stent which is positioned over the balloon, the axially oriented forces which retain the stent on the balloon catheter are enhanced.

For the manufacture of the stent delivery system of the present invention, several pre-processing steps are involved. First, the balloon of a balloon catheter is folded to establish a low profile for the balloon. Preferably, this folding results in a well known S-fold configuration for the balloon. This S-fold profile is then further reduced by drawing a vacuum on the balloon. Next, a tubular sleeve is placed over the balloon in order to maintain the balloon's minimized S-fold configuration. The S-folded balloon is then heated inside the tubular sleeve to a temperature that is slightly below the melt transition temperature of the balloon material. This heating is continued for approximately five minutes in order to establish a permanent set for the S-fold in the balloon. The pre-processing steps of the methods for the present invention are finally completed by cooling the balloon and removing the tubular sleeve therefrom.

After being pre-processed, an expandable stent is crimped onto the balloon to create a balloon-stent assembly. Preferably this is done using a double acting crimpers. For purposes of the present invention, it will be understood the stent itself may be either a wire coil type stent or a tubular type stent. In either case, the stent will somehow be formed with openings in its wall, such as spaces between portions of the wire in the case of a wire coil stent, or holes in the case of a tubular stent.

Once the stent has been crimped over the balloon, a thin-walled teflon tube is placed over the stent to constrain the balloon-stent assembly. Specifically, this teflon tube is formed with a longitudinally oriented slit which allows the tube to accommodate dimensional variations along the length of the balloon-stent assembly. A shrink wrap tube is then positioned around the teflon tube and over the balloon-stent assembly. This shrink wrap is then shrunk to constrain the tube on the balloon-stent assembly and thereby limit any substantial expansion of the stent due to an inflation of the balloon.

The balloon inside the constrained balloon-stent assembly is pressurized with an inflation pressure in the range of approximately ten to twelve pounds per square inch (10–12 psi.). This pressurized balloon-stent assembly is then heated. Specifically, the balloon-stent assembly is then heated to a temperature which is again slightly below the melt transition temperature of the balloon material, and this heating is continued for approximately five minutes. During this heating step the balloon is permanently deformed to create protrusions on the balloon's surface which are inserted into the openings of the stent. In this manner, the stent is embedded into the balloon to help retain the stent on the balloon. Upon completion of this heating step, the balloon-stent assembly is allowed to cool to room temperature and the shrink wrap and slit teflon tube are then removed.

The result of the process methods of the present invention set forth above is a stent delivery system which includes a balloon that has been reconfigured to conform with irregularities in the wall of a stent. Due to this reconfiguration of the balloon, a structural interaction between the balloon and stent is achieved which enhances the retention forces that help hold the stent on the balloon until the stent can be delivered and placed at a lesion site in a patient. More specifically, protrusions formed on the balloon surface are inserted into openings in the stent wall to establish a resistive (retention) force having a direction that is substantially aligned with the longitudinal axis of the stent, and a magnitude that is greater than approximately three tenths of a Newton.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a stent delivery system in accordance with the present invention;

FIG. 2 is an exploded perspective view of a balloon in an S-fold configuration with a tubular sleeve positioned to be placed over the balloon;

DESCRIPTION OF THE PREFERRED EMBODIMENT

Figure 3:
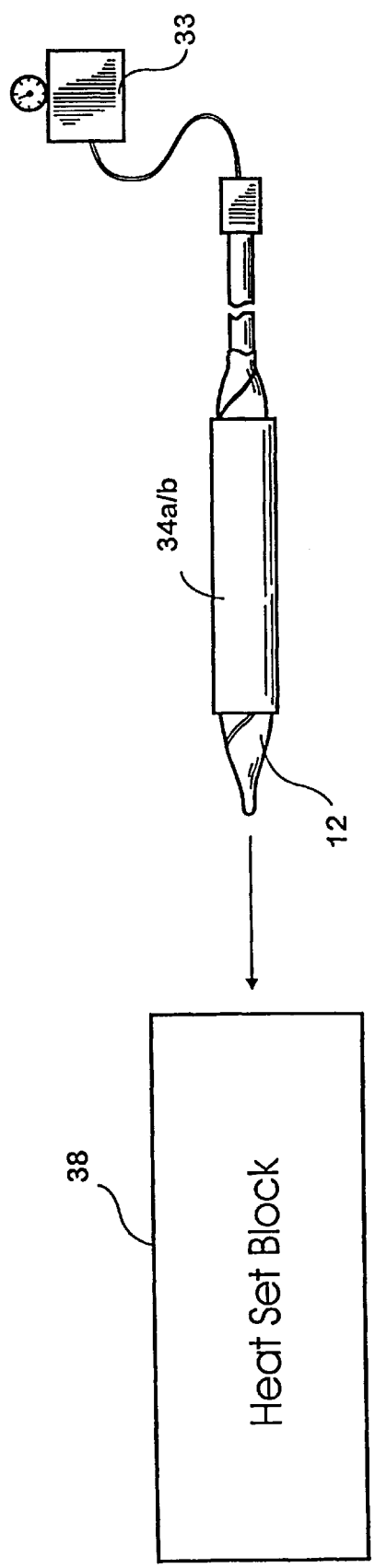
FIG. 3 is a schematic representation of a constrained balloon assembly with the heating and pressurizing equipment that are used in the processes of the present invention.

Referring initially to FIG. 1 a stent delivery system in accordance with the present invention is shown and generally designated 10. In FIG. 1 it will be seen that the system 10 includes a balloon 12, and a stent 14 which is positioned to surround the balloon 12 substantially as shown. Additionally, the system 10 includes a catheter 16 which has an inflation port 18 at the proximal end of the catheter 16. A pump 20, is connectable in fluid communication with the inflation port 18 and, via an inflation lumen in the catheter 16 (not shown), the pump 20 is also in fluid communication with the balloon 12 for the purpose of selectively inflating the balloon 12. For purposes of the present invention the balloon 12 may be made of any suitable material known in the pertinent art, such as polyethylene, polypropylene, polyvinylchloride (PVC) or polyethylene terephthalate (PET). Other materials such as Teflon, polyurethane, Nylon, and Pebrx may also be suitable.

Still referring to FIG. 1 it can be appreciated that the stent 14 defines a lumen 22 which, as shown in FIG. 1, is occupied by the balloon 12. Also, it can be seen that the stent 14 comprises a plurality of elements 24, of which the elements 24a–d are only exemplary. As shown, the elements 24 of stent 14 are distanced from each other so as to form openings 26 therebetween. Of these, the openings 26a–c are also only exemplary. As will become more apparent in light of the disclosure below, the plurality of openings 26 which are established between the various elements 24 of stent 14 are occupied by a respective protrusion 28 of the balloon 12. In accordance with the present invention, as the protrusions 28 are formed, they become inserted into the openings 26. With this structure, the inserted protrusions 28 of balloon 12 are able to interact with the elements 24 of the stent 14 to enhance retention forces between the balloon 12 and the stent 14. Specifically, the protrusions 28 interact with the stent 14 to inhibit relative movement between the balloon 12 and the stent 14 along their mutually coaxial directions indicated by the arrows 30. The protrusions 28 thereby help prevent the stent 14 from prematurely slipping off the balloon 12.

For the purposes of the present invention it is to be appreciated that the stent delivery system 10 can accommodate either of the two commonly used classes of balloon-expandable stents 14 that are recognized in the pertinent art. One class of these stents are tube stents which are cut from a tube of metal. Typically, this is done by lasers. The other class of stent includes stents, like the stent 14 shown in the FIGS. 4–7, which are made by winding a wire into a cylindrical shape. Importantly, whatever class of stent 14 is used, the stent 14 must somehow be formed with openings 26. In all other respects, insofar as the present invention is concerned, the differences between different stents 14 is immaterial. Further, it is to be appreciated that the stent 14 may be made of any suitable material well known in the pertinent art, such as tantalum, stainless steel, or Nitinol. Further, it is to be appreciated that the surface of the stent 14 may be roughened or etched to present a textured surface. Alternatively, the surface of stent 14 may be smooth.

To begin the manufacture of the stent delivery system 10 of the present invention, it is first necessary to pre-process the balloon 12. First, as shown in FIG. 2, the balloon 12 is preferably twisted with an S-fold 32 in order to minimize its profile. At this point it should be mentioned that other commonly used folds, such as the "tri-fold" or the "taco fold", are also useable. In any case, after the balloon 12 has been configured with an S-fold 32, it is connected via the catheter 16 to a pump 33 as shown in FIG. 3. For this step in the methods of the present invention, the pump 33 is used as a vacuum pump and a vacuum is then drawn in the balloon 12 to further minimize the balloon profile. As perhaps best appreciated in FIG. 2, but also indicated in FIG. 3, a tubular sleeve 34a is positioned over the balloon 12. This is done while the balloon 12 is in its S-fold configuration. Preferably, the tubular sleeve 34 is made of teflon and is formed with a longitudinal slit 36 (see FIG. 2) to facilitate the positioning of the sleeve 34a over the S-folded balloon 12.

Once the tubular sleeve 34a is in place on the balloon 12, the combination is placed in a heat set block 38, as indicated in FIG. 3. There it is heated to a temperature slightly above the melt transition temperature for the material of the balloon 12. For example, the melt transition temperature for a polyethylene material suitable for the balloon 12 of the system 10 is around ninety five degrees Centigrade (95° C.). In any event, the balloon 12 is heated at this temperature for approximately five minutes in order to establish a permanent set for the balloon 12. Specifically, with this heat set the balloon 12 will return to its S-fold configuration whenever the balloon 12 is deflated. After the approximately five minutes of heating, the balloon 12, with tubular sleeve 34a, is removed from the heat set block 38, cooled to room temperature, and the tubular sleeve 34a is then removed. At this point the pre-processing of the balloon 12 has been completed.

Figure 4:
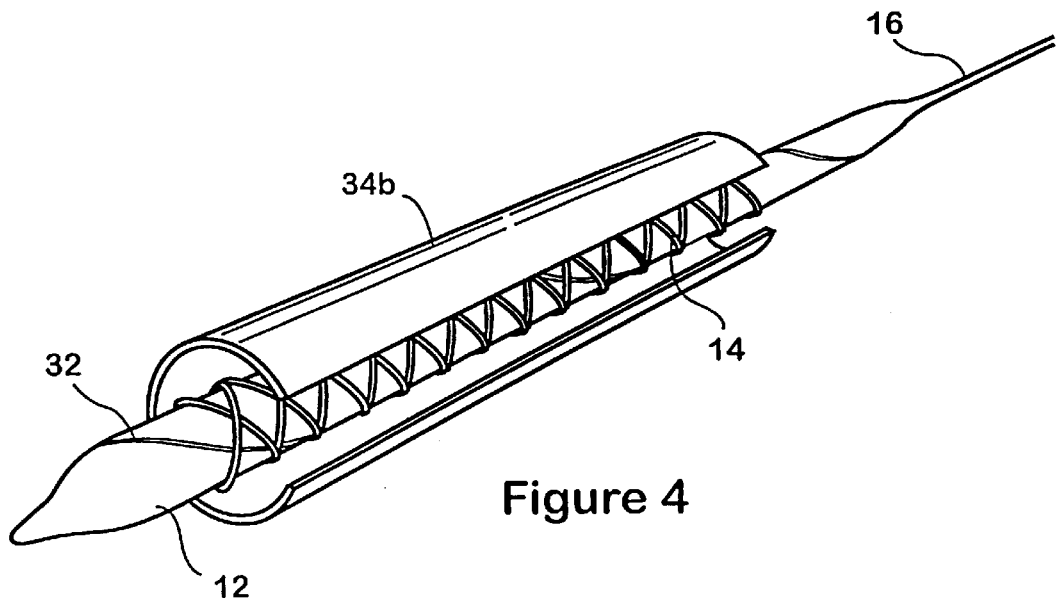
FIG. 4 is a perspective view of the distal end portion of a balloon catheter with a stent mounted on the balloon and with the balloon-stent assembly positioned inside a slit tube.

After the balloon 12 has been preprocessed, a stent 14 is crimped onto the balloon 12 as shown in FIG. 4. The actual crimping of the stent 14 onto the balloon 12 can be accomplished in any manner well known in the pertinent art. Preferably this is done by using a tool commonly called a double crimpers. As shown, the stent 14 is positioned on the balloon 12 so that the longitudinal axis of the stent 14 is substantially coaxial with the longitudinal axis of the balloon 12.

Once the stent 14 has been positioned on the balloon 12 to create a balloon-stent assembly 12/14, a tubular sleeve 34b is placed over the balloon-stent assembly 12/14 to constrain the stent 14 on the balloon 12. For purposes of the present invention, the tubular sleeve 34b is preferably made of Teflon and is substantially similar to the tubular sleeve 34a discussed above. In fact, it may be that the tubular sleeve 34b now used to constrain the balloon-stent assembly 12/14 is the very same tubular sleeve 34a that was previously used for setting the S-fold in the balloon 12.

Figure 5A:
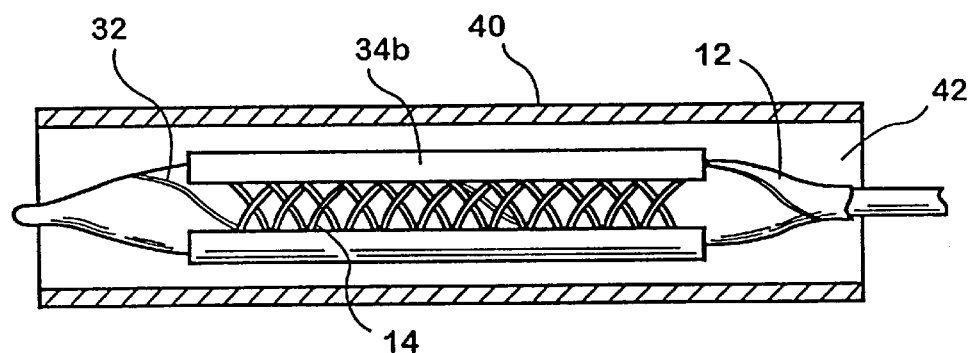
FIG. 5A is a side view of the balloon-stent assembly inside the tube and a cross sectional view of a shrink wrap positioned thereover.
Figure 5B:
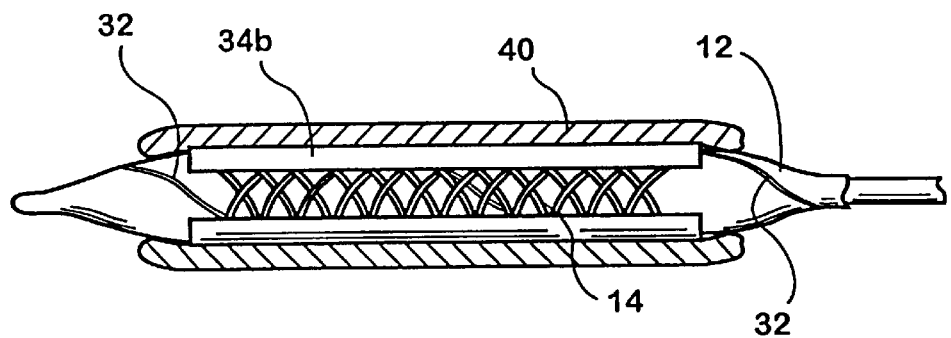
FIG. 5B is a view of the balloon-stent assembly as in FIG. 5A with the shrink wrap shrunk onto the balloon-stent assembly.

FIG. 5A shows that the next step in the method for manufacturing the stent delivery system 10 is to position a shrink wrap 40 over the tubular sleeve 34b on the balloon-stent assembly 12/14. For purposes of the present invention, the shrink wrap 40 may be made of any appropriate material well known in the pertinent art. As indicated in FIG. 5A, the shrink wrap 40 is substantially a tubular structure that forms a lumen 42 which receives therein the balloon-stent assembly 12/14 as it is being constrained by the tubular sleeve 34b. With the balloon-stent assembly 12/14 positioned inside the lumen 42 of shrink wrap 40, the shrink wrap 40 is then heated to shrink the shrink wrap 40 onto the balloon-stent assembly 12/14 as shown in FIG. 5B. Thus, the shrink wrap 40 will act in concert with the tubular sleeve 34b to constrain the balloon-stent assembly 12/14 in response to an inflation of the balloon 12.

Returning to FIG. 3 it will be seen that the balloon-stent assembly 12/14, while constrained by the tubular sleeve 34b and the shrink wrap 40, is placed into the heat set block 38. Either before this combination is placed into the heat set block 38, or after the combination is so place, the balloon 12 is pressurized by the pump 33 to an inflation pressure of approximately ten to twelve pounds per square inch (10–12 psi). At this pressure, the constrained balloon-stent assembly 12/14 is heated in the heat set block 38 to a temperature that is slightly below the melt transition temperature of the balloon 12. As indicated above, for a polyethylene material this temperature will be around approximately ninety five degrees Centigrade (95° C.). The constrained balloon-stent assembly 12/14, while remaining pressurized at 10–12 psi., is heated in the heat set block 38 for approximately five minutes and then removed.

Figure 6:
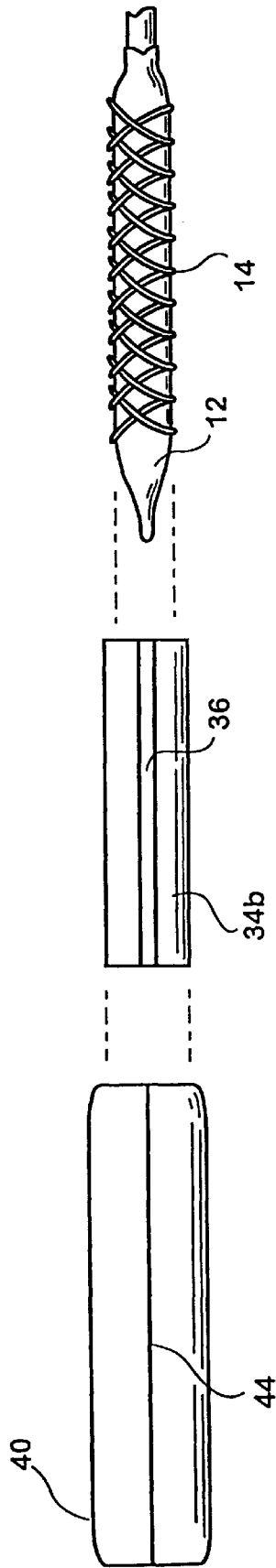
FIG. 6 is an exploded view of the shrink wrap, tube, and balloon-stent assembly of the present invention after a heating step.

FIG. 6 shows that after the balloon-stent assembly 12/14 has been depressurized and cooled to room temperature, the shrink wrap 40 is cut along the line 44 and removed. Next, the tubular sleeve 34b is removed. This leaves the stent 14 still positioned on the balloon 12.

Figure 7A:
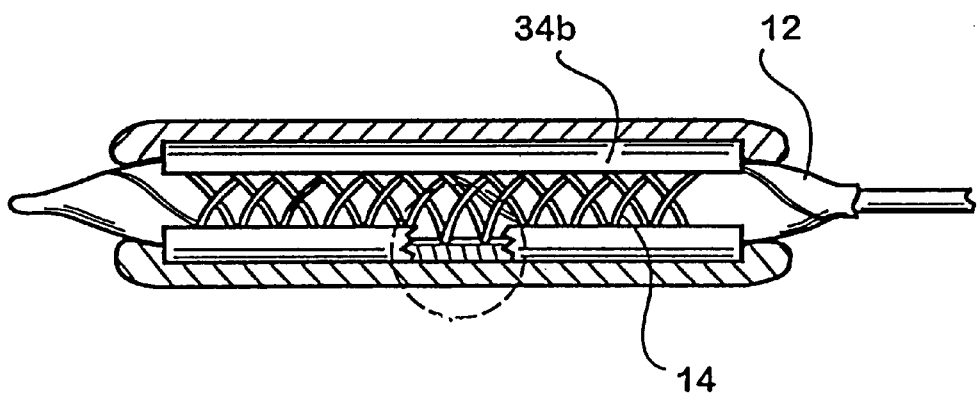
FIG. 7A is a view as in FIG. 5B with portions broken away for clarity.
Figure 7B:
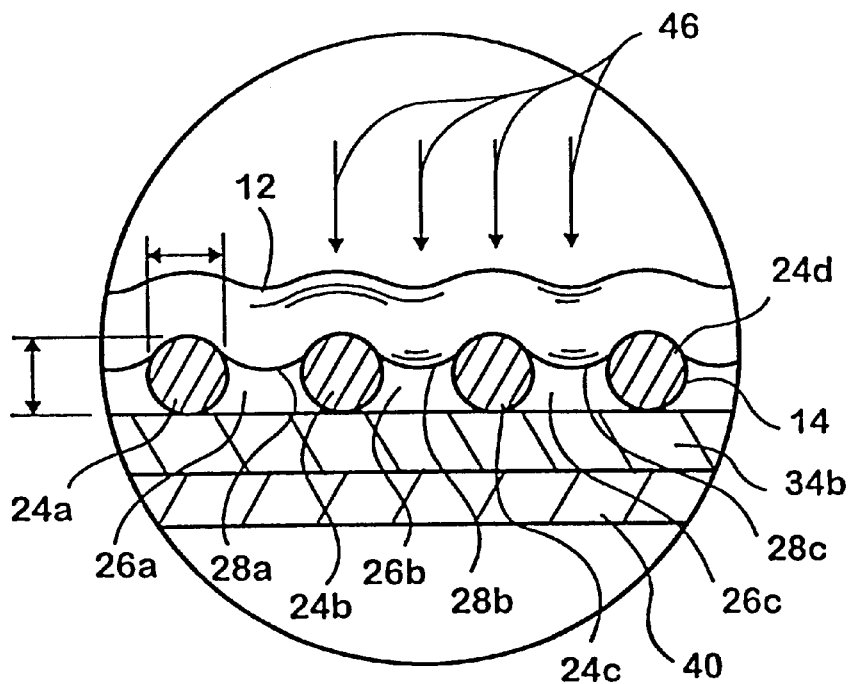
FIG. 7B is an isolated cross sectional view of the broken away portion shown in FIG. 7A.

The structure for balloon 12 which results from the pressurized heating step disclosed above is, perhaps, best appreciated by cross-referencing FIGS. 7A and 7B. In these Figures it will be seen that by subjecting the balloon 12 to an inflation pressure which acts in the directions indicated by the arrows 46, while heating the balloon 12 at a temperature which is slightly below its melt transition temperature, protrusions 28 of balloon 12 are permanently formed in the openings 26 of stent 14. These protrusions 28 will then remain inserted into the openings 26 after the combination is subsequently retrieved from the heat set block 38 and cooled to room temperature.

It is to be appreciated that the disclosure here is adaptable to any class of stent 14. Although a wire stent 14 has been illustrated, the stent 14 could just as easily have been a tube stent 14. For example, in FIG. 7B the element 24a of the stent 14 is shown to have a width 48 and a thickness 50. There is, however, no limitation intended for the relative sizes for the width 48 and the thickness 50. Where they are equal, as here, it is a wire stent 14. The result in any case, after removal of the shrink wrap 40 and the tubular sleeve 34b, is the stent delivery system 10 shown in FIG. 1.

While the particular heat set and crimping process to optimize stent retention as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for manufacturing a stent delivery catheter which comprises the steps of:

crimping an expandable stent over an inflatable balloon to create a balloon-stent assembly, the stent having a plurality of elements defining a lumen for receiving the balloon therein, each element having a width and a thickness with at least one opening defined by said elements;

positioning a tubular covering around the balloon-stent assembly to accommodate the balloon-stent assembly inside the tubular covering;

shrinking a shrink wrap onto the tubular covering to limit any substantial expansion of the tubular covering to constrain the balloon-stent assembly inside the tube;

pressurizing the constrained balloon-stent assembly with an inflation pressure;

heating the pressurized balloon-stent assembly to permanently deform the balloon and embed the stent into the balloon to retain the stent on the balloon; and removing the shrink wrap and the tubular covering from the balloon-stent assembly.

2. A method as recited in claim 1 wherein said pressurizing step is accomplished using an inflation pressure of ten to twelve pounds per square inch (10–12 psi).

3. A method as recited in claim 1 wherein the balloon has a melt transition temperature, and said heating step is accomplished at a temperature below the melt transition temperature of the balloon for a time duration of approximately five minutes.

4. A method as recited in claim 3 wherein the melt transition temperature is approximately ninety five degrees Centigrade (95° C.).

5. A method as recited in claim 1 further comprising the step of cooling the stent-balloon assembly to room temperature after said heating step.

6. A method as recited in claim 1 wherein said crimping step is accomplished using a double acting crimpers.

7. A method as recited in claim 1 further comprising the pre-processing steps of:

folding the balloon with an S-fold configuration;

drawing a vacuum in the balloon to minimize the balloon profile in the S-fold configuration;

placing a tubular sleeve over the balloon to maintain the minimized S-fold configuration;

heating the sleeved balloon to cause a permanent setting of the S-fold configuration in the balloon; and removing the sleeve.

8. A method as recited in claim 1 wherein said tubular sleeve is formed with a longitudinal slit to facilitate said positioning step.

9. A method of manufacturing a stent delivery catheter which comprises the steps of:

crimping an expandable stent over an inflatable balloon to create a balloon-stent assembly, the stent having a plurality of elements defining a lumen for receiving the balloon therein. each element having a width and a thickness with at least one opening defined by said elements;

positioning a tubular covering around the balloon-stent assembly to accommodate the balloon-stent assembly inside the tubular covering, wherein said tubular sleeve is formed with a longitudinal slit to facilitate said positioning step;

shrinking a shrink wrap onto the tubular covering to limit any substantial expansion of the tubular covering to constrain the balloon-stent assembly inside the tube;

pressuring the constrained balloon-stent assembly with an inflation pressure in the range of ten to twelve pounds per square inch (10–12 psi);

heating the pressurized balloon-stent assembly with a temperature below the melt transition temperature of the balloon for a time duration of approximately five minutes to permanently deform the balloon and embed the stent into the balloon to retain the stent on the balloon; and removing them shrink wrap and tubular covering from the balloon-stent assembly.

* * * * *